(12) United States Patent
Schultheiss

(10) Patent No.: US 8,092,401 B2
(45) Date of Patent: Jan. 10, 2012

(54) METHOD AND APPARATUS FOR PRODUCING SHOCK WAVES FOR MEDICAL APPLICATIONS

(75) Inventor: Reiner Schultheiss, Illighausen (CH)

(73) Assignee: Sanuwave, Inc., Alpharetta, GA (US)

( * ) Notice: Subject to any disclaimer, the term of this patent is extended or adjusted under 35 U.S.C. 154(b) by 1703 days.

(21) Appl. No.: 10/176,647

(22) Filed: Jun. 24, 2002

(65) Prior Publication Data
US 2003/0028129 A1 Feb. 6, 2003

(30) Foreign Application Priority Data
Jun. 26, 2001 (DE) .................. 101 30 639

(51) Int. Cl.
*A61N 7/00* (2006.01)
(52) U.S. Cl. .................. 601/2; 601/3; 601/4
(58) Field of Classification Search .............. 601/2–4
See application file for complete search history.

(56) References Cited

U.S. PATENT DOCUMENTS

| | | | |
|---|---|---|---|
| 2,559,227 A | 7/1951 | Rieber | 601/4 |
| 3,105,456 A | 10/1963 | Gongwer | 116/27 |
| 4,543,293 A | 9/1985 | Nakamura et al. | 428/421 |
| 4,721,106 A | 1/1988 | Kurtze et al. | 128/328 |
| 4,879,993 A * | 11/1989 | Reichenberger et al. | 601/4 |
| 4,972,826 A * | 11/1990 | Koehler et al. | 601/4 |
| 5,156,144 A * | 10/1992 | Iwasaki et al. | 601/4 |
| 5,649,338 A * | 7/1997 | Kato | 15/304 |
| 5,788,496 A * | 8/1998 | Marlinghaus | 433/215 |
| 6,036,661 A * | 3/2000 | Schwarze et al. | 601/4 |
| 6,592,545 B1 * | 7/2003 | Bellhouse et al. | 604/69 |
| 6,719,449 B1 * | 4/2004 | Laugharn, Jr. et al. | 366/127 |
| 6,736,784 B1 | 5/2004 | Menne et al. | 601/2 |
| 6,755,796 B2 * | 6/2004 | Spector | 601/2 |
| 6,948,843 B2 * | 9/2005 | Laugharn, Jr. et al. | 366/127 |
| 2002/0022827 A1 * | 2/2002 | Esch et al. | 606/7 |
| 2003/0194473 A1 * | 10/2003 | Redding et al. | 426/238 |

FOREIGN PATENT DOCUMENTS

| | | | |
|---|---|---|---|
| DE | 7738704 | 12/1977 | |
| DE | 3312014 | 10/1984 | 17/22 |
| DE | 199 19 430 C1 | 10/2000 | |
| WO | WO 90/10419 | 9/1990 | 17/22 |

* cited by examiner

*Primary Examiner* — Tse Chen
*Assistant Examiner* — Baisakhi Roy
(74) *Attorney, Agent, or Firm* — Hunton & Williams LLP

(57) ABSTRACT

The invention describes a method and an apparatus for producing shock waves in a fluid for medical applications. In a work volume filled with fluid, the pressure is increased mechanically by pulses. The pressure pulse produced in the work volume is transferred to the fluid volume by means of a partition, in order to produce shock waves in the fluid volume.

4 Claims, 2 Drawing Sheets

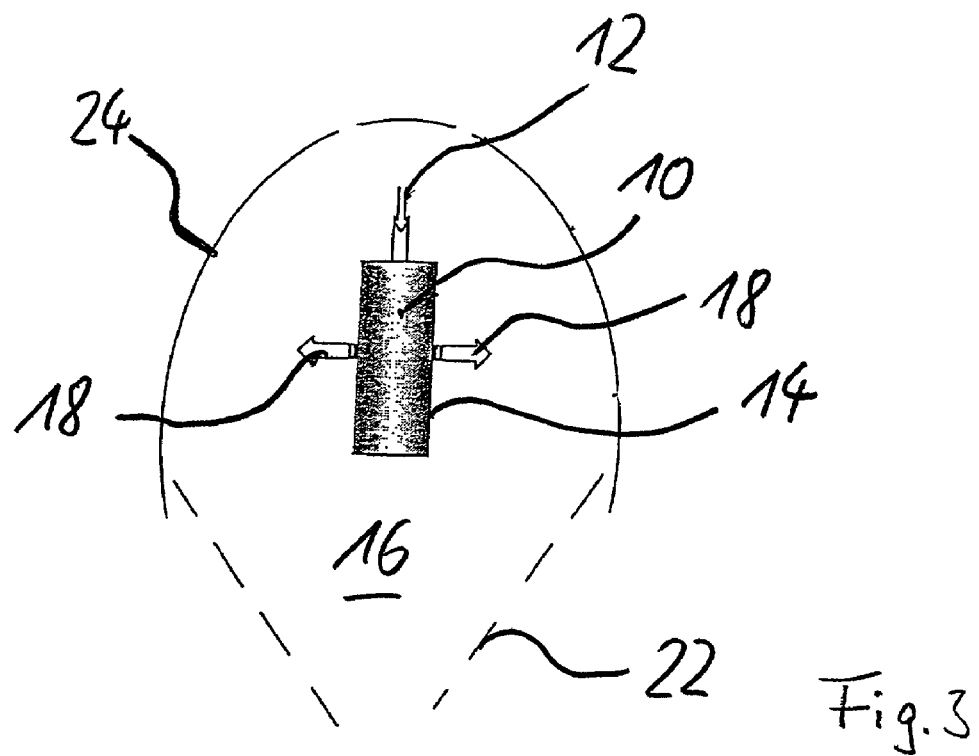

METHOD AND APPARATUS FOR PRODUCING SHOCK WAVES FOR MEDICAL APPLICATIONS

BACKGROUND OF THE INVENTION

The invention relates to a method and an apparatus for producing shock waves for medical applications.

For various medical indications, shock waves are used that are produced in a fluid volume and focused on the areas of the patient to be treated. Various methods and apparatuses are known for producing the shock waves.

In one embodiment, the shock waves are produced by electromagnetic means. An electrical impulse in a coil is used to a deflect a diaphragm by producing a pressure pulse in the adjacent fluid volume. If the coil is a flat coil, this produces an even pressure wave, which is focused by means of acoustic lenses located in the fluid volume. If the coil and the membrane are curved, then the pressure wave that is produced is focused by the curved diaphragm surface. If a cylindrical coil is used, the cylindrically expanding pressure wave is reflected and focused by a correspondingly shaped rotation surface.

A further known method for producing the pressure waves is to use piezoelectric elements. The piezoelectric elements can be located on a rotation surface, so that pressure waves produced by these elements are focused.

Finally, a method is known to produce the shock waves by electro hydraulic means. In this process, an electric spark discharge is ignited in the fluid volume, which produces a plasma bubble. The shock wave, which expands spherically, is focused by reflecting on suitable rotation surfaces.

In all of these known methods, the shock wave is triggered by an electrical impulse. The required electrical impulses generally are characterized by short rise times and high energy, so that electromagnetic shielding problems arise, which can have adverse effects, especially in the presence of further electrical devices or patient-related apparatuses e.g. pacemakers. Some of the known devices also display high electrical power dissipation, which necessitates expensive cooling systems. Consequently, there exist an unfulfilled need for a method and an apparatus for producing shock waves for medical application, which ensures better degree of efficiency and less electromagnetic shielding problems.

BRIEF SUMMARY OF THE INVENTION

The underlying idea of the invention consists in producing a pressure pulse by mechanical means in a work space filled with fluid and transferring this pressure pulse to the fluid, in order to produce the shock wave in this fluid. To produce the pressure pulse in the work space, a fluid can be injected under high pressure into the work space, as for example in the process of injection used in diesel engines. Another object of the invention is to allow a piston moved by mechanical means to act upon the volume of the work space in order to increase the pressure in the work space by pulses.

The work space and the fluid volume in which the pressure wave is produced are separated by a partition. Preferably, a closed partition is used that can be moved, e.g. on bearings, or made of a flexible material. The pressure increase in the work space causes a displacement in the partition, which in turn produces the shock wave in the adjacent fluid volume. It is also possible to use a partition with openings. The pressure increase by pulses in the work space causes the fluid to be pressed from the work space through the openings of the partition into the fluid. The fluid, which penetrates the fluid volume under pressure, produces pressure waves in the fluid, which build up the desired shock waves.

The form of the partition enables different ways of producing pressure waves in the fluid volume, which said pressure waves form shock waves in the fluid and are focused in a suitable manner. In principal, the same geometrical arrangements can be used for this purpose as the state of the art used for shock waves produced by electrical means.

BRIEF DESCRIPTION OF THE DRAWING

These and other features, aspects and advantages of the present invention will become better understood with reference to the following description, appended claims, and accompanying drawing, where:

FIG. 3 depicts is a schematic representation of a design, in which the work space has a cylindrical shape and is located in the fluid volume

Figure 1:
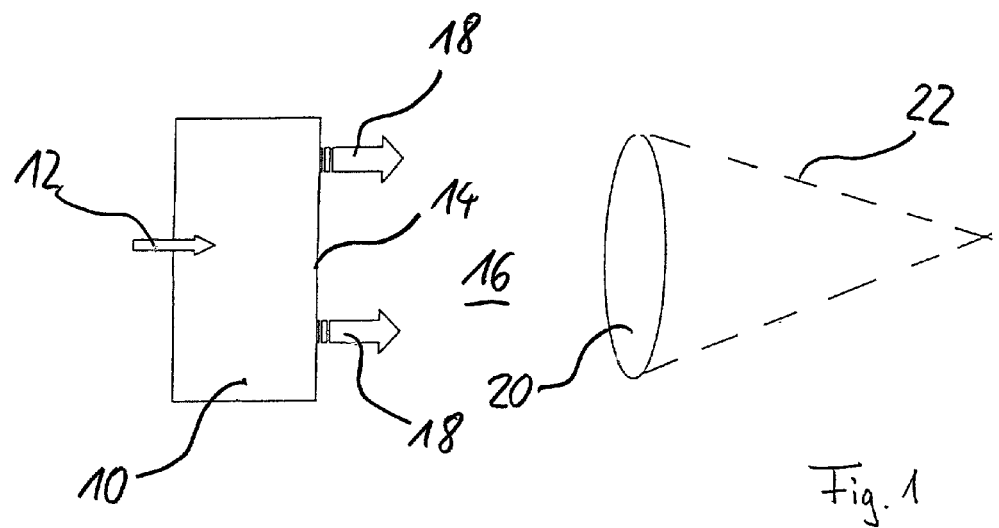
FIG. 1 depicts a schematic representation of an apparatus designed in accordance with the invention.

LIST OF REFERENCE NUMBERS 10 work space
12 arrow for pressure increase
14 partition
16 fluid volume
18 arrows for pressure transfer
20 acoustic lens
22 focus
24 reflector In the drawing, the principle of producing the shock waves is depicted only schematically. Equivalent parts are indicated by the same reference numbers.

DETAILED DESCRIPTION OF THE INVENTION

The invention summarized above and defined by the enumerated claims may be better understood by referring to the following detailed description, which should be read in conjunction with the accompanying drawing. This detailed description of a particular preferred embodiment, set out below to enable one to practice the invention, is not intended to limit the enumerated claims, but to serve as a particular example thereof.

FIG. 1 illustrates a closed work space 10, which is filled with a fluid. The fluid can be a gas or a liquid. As symbolized by an arrow 12, the pressure in the work space 10 is increased by pulses by mechanical means. For this purpose, a liquid can be injected under high pressure into the work space 10, as for example in the injection pumps of a diesel engine. Alternatively, the volume of the work space 10 can be acted upon by a piston that is moved mechanically, in order to increase the pressure in the work space 10.

The work space 10 is separated by a partition 14 from a fluid volume 16, in which the shock waves are produced. In the sample embodiment of FIG. 1, the partition 14 is designed as a flat partition. The partition 14 can be a more or less rigid plate, e.g. made of metal or plastic, which is mounted flexibly, thus making it moveable. Likewise, the partition 14 can be made of a flexible material, so that it can bend and move.

The pressure increase by pulses in the work space 10 causes a deflection of the partition 14, as symbolized by the arrows 18. The deflection of the partition 14 produces an even pressure wave in the fluid volume 16, which said pressure
} wave increases to a shock wave during the expansion in the fluid volume 16. The shock wave is focused by means of an acoustic lens 20, as indicated by the broken lines 22.

The partition 14 can alternatively be designed as a rigid wall that is interrupted by openings uniformly distributed on a grid. In this case, the pressure increase by pulses in the work space 10 causes the fluid, preferably a liquid, to be pressed under pressure through the openings of the partition 14 into the fluid volume 16. The fluid streams penetrating the individual openings produce spherical pressure waves in the fluid volume 16, which combine to an even pressure wave due to the uniform distribution of the openings in the partition 14.

Figure 2:
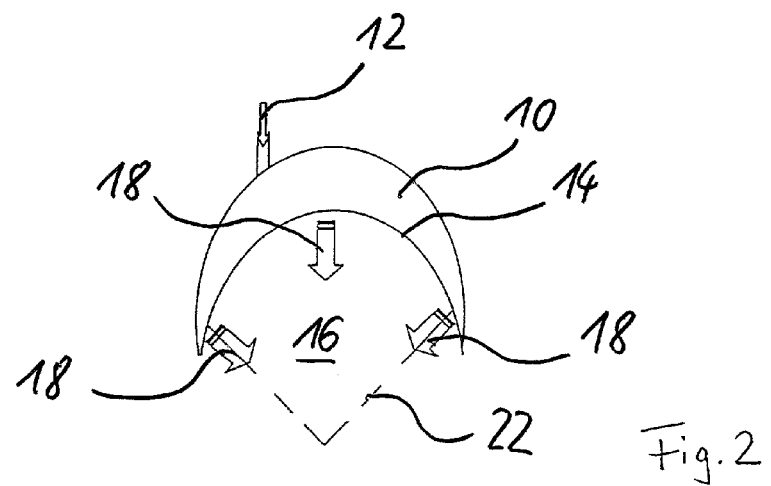
FIG. 2 depicts a schematic representation of a design in which, the partition is designed as a focusing rotation surface

FIG. 2 shows a design in which, the partition 14 separates the work space 10 from the fluid volume 16, designed as a focusing rotation surface, e.g. as a rotation parabola or rotation ellipsoid, which partially encloses the fluid volume 16. Here also the partition 14 can be flexible, flexibly mounted or provided with openings in a grid. If the pressure in the work space 10 is increased by pulses, as indicated by the arrow 12, then the partition 14 is deflected or fluid streams penetrate the openings of the partition 14 into the fluid volume 16. This produces pressure waves in the fluid volume 16, which said pressure waves produce a focused shock wave due to the focusing surface form of the partition 14.

FIG. 3 shows a design, in which the work space 10 has a cylindrical shape and is located in the fluid volume 16. The partition 14 forms the surface area of the cylindrical work space 10. The fluid volume 16 is partially enclosed by a reflector 24, which is designed as a focusing rotation surface.

If the pressure in the work space 10 is increased by pulses, then the flexible partition 14 is deflected radially, producing a cylindrically expanding pressure wave, which is focused by means of the reflector 24. Here also the cylinder surface area of the partition 14 can alternatively be rigid and provided with openings, so that fluid streams can be pressed through the surface area of the partition 14 into the fluid volume in order to produce the cylindrical pressure wave.

The work space 10 in this embodiment can be designed as a double-walled hollow cylinder, whereby the outer surface area forms the partition 14 and a rigid inner surface area forms a cylindrical interior area in which, for example, the head of a diagnostic device can be inserted or in which irradiation by X-rays or ultrasonic waves is possible.

What is claimed is:

1. A method for medically treating a patient by producing shock waves in a surrounding fluid adjacent a work volume comprising the steps of:
   increasing pressure in fluid of the work volume by mechanical pulses;
   deflecting by at least one of moving and bending a partition separating the surrounding fluid adjacent the work volume from the fluid of the work volume with the pulses;
   generating pulses of shock waves in the surrounding fluid and outward from the work volume from repeatedly deflecting the partition; and
   applying generated pulses of shock waves to an area of a patient for medical treatment.

2. A method according to claim 1, further comprising injecting a fluid into the work volume to increase the pressure in the work volume.

3. A method according to claim 1, further comprising pistoning the work volume to increase the pressure in the work volume.

4. A method for medically treating a patient by producing shock waves in a surrounding fluid adjacent a work volume comprising the steps of:
   increasing mechanically pressure in a work volume filled with fluid by mechanical pulses;
   pressing with the pulses fluid from the work volume as separate individual fluid streams through a plurality of predefined individual openings in a partition separating the surrounding fluid adjacent the work volume from the fluid of the work volume;
   generating pulses of shock waves in the surrounding fluid and outward from the work volume from repeatedly pressing fluid through the plurality of individual openings; and
   applying generated pulses of shock waves to an area of a patient for medical treatment.

* * * * *